United States Patent [19]

Nakayama et al.

[11] 4,169,763

[45] Oct. 2, 1979

[54] PROCESS FOR THE PRODUCTION OF L-LYSINE BY FERMENTATION

[75] Inventors: Kiyoshi Nakayama, Sagamihara; Kazumi Araki; Yoshitake Tanaka, both of Machida, all of Japan

[73] Assignee: Kyowa Hakko Kogyo Co., Ltd., Japan

[21] Appl. No.: 814,621

[22] Filed: Jul. 11, 1977

[30] Foreign Application Priority Data

Jul. 9, 1976 [JP] Japan .................................. 51-81016

[51] Int. Cl.² ............................................. C12D 13/06
[52] U.S. Cl. ..................................... 435/115; 435/843
[58] Field of Search .................................... 195/29, 47

[56] References Cited

U.S. PATENT DOCUMENTS

| 2,979,439 | 4/1961 | Kinoshita et al. ...................... 195/47 |
| 3,687,810 | 8/1972 | Kurihara et al. ....................... 195/29 |
| 3,819,483 | 6/1974 | Yoshinaga et al. ..................... 195/29 |
| 3,905,867 | 9/1975 | Kurimura et al. .................. 195/28 R |
| 3,959,075 | 5/1976 | Inuzuka et al. .......................... 195/29 |
| 4,066,501 | 1/1978 | Tosaka et al. ........................... 195/29 |

*Primary Examiner*—Lionel M. Shapiro
*Attorney, Agent, or Firm*—Craig and Antonelli

[57] ABSTRACT

A process for producing L-lysine by fermentation includes the steps of culturing a strain belonging to the genus Corynebacterium having both an ability to produce L-lysine and a resistance to at least one member selected from the group consisting of aspartic acid analogs and sulfa drugs in a nutrient medium, forming and accumulating L-lysine in the resulting culture liquor and thereafter recovering the L-lysine therefrom.

6 Claims, No Drawings

PROCESS FOR THE PRODUCTION OF L-LYSINE BY FERMENTATION

This invention relates to a process for producing L-lysine by fermentation. More specifically, the present invention relates to a process for producing L-lysine by fermentation, characterized by culturing a strain belonging to the genus Corynebacterium and having both an ability to produce L-lysine and a resistance to at least one member selected from the group consisting of aspartic acid analogs and sulfa drugs in a nutrient medium, and recovering L-lysine formed and accumulated from the culture liquor.

L-lysine is one of essential amino acids well known in the art, and has a great demand as a medicament, or an additive to animal feed or food.

Heretofore, the following processes have been known as the processes for producing L-lysine by fermentation: Processes using homoserine (or methionine and threonine)—requiring mutants (U.S. Pat. No. 2,979,439) or mutants having a nutritional requirement for threonine, methionine, arginine, histidine, leucine, isoleucine, phenylalanine, cystine, or cysteine (U.S. Pat. No. 3,700,557), processes using a mutant having a resistance to lysine analog (U.S. Pat. No. 3,707,441), a mutant having both an ability to produce L-lysine and a resistance to bacitracin, penicillin G or polymyxin (U.S. Pat. No. 3,687,810) and processes using mutants having a nutritional requirement for homoserine, threonine, threonine and methionine, leucine, isoleucine or mixtures thereof and a resistance to lysine, threonine, isoleucine or analogs thereof (U.S. Pat. No. 3,708,395), a mutant having a resistance to lysine analog and a nutritional requirement for serine, proline, alanine, nicotinamide, nicotinic acid, pantothenic acid, thiamine, guanine, adenine, hypoxanthine, vitamine $B_{12}$ (U.S. Pat. No. 3,825,472).

As a result of various studies for obtaining strains having an improved L-lysine productivity in view of recently increasing demand for L-lysine, the present invention have found that a strain capable of producing L-lysine belonging to the genus Corynebacterium endowed with a resistance to at least one member selected from the group consisting of aspartic acid analogs and sulfa drugs has a remarkably improved ability to produce L-lysine, and have completed the present invention.

A fact of the improvement in productivity of L-lysine by using a strain having a resistance to at least one member selected from the group consisting of aspartic acid analogs and sulfa drugs in the production of L-lysine by fermentation has been found by the present inventors first.

The present invention is explained in detail below.

In the present process, any strain may be used so long as it belongs to the genus Corynebacterium and has both an ability to produce L-lysine and a resistance to at least one member selected from the group consisting of aspartic acid analogs and sulfa drugs. That is, in the present invention, either a strain belonging to the genus Corynebacterium and having an ability to produce L-lysine to which a resistance to at least one member selected from the group consisting of aspartic acid analogs and sulfa drugs is endowed, or a strain belonging to the genus Corynebacterium and having a resistance to at least one member selected from the group consisting of aspartic acid analogs and sulfa drugs to which an ability to produce L-lysine is endowed may be used. As the strain belonging to the genus Corynebacterium and having an ability to produce L-lysine, for example, strains capable of producing L-lysine having one or a combination of a requirement for nutrients (for example, homoserine, methionine, threonine, histidine, proline, alanine, leucine, isoleucine, valine, serine, pantothenic acid, nicotinic acid, nicotinic acid amide, thiamine, adenine, hypoxanthine and their combinations), a resistance to various amino acid analogs (for example, analogs of lysine, threonine, methionine, leucine, isoleucine, valine, or histidine, and their combinations), and a resistance to other chemicals (for example, various antibiotics such as penicillin G, polymyxin, bacitracin, and their combinations, etc.) may be mentioned. Accordingly, a strain to be used in the present invention may be obtained by endowing a property of resistance to at least one member selected from the group consisting of aspartic acid analogs and sulfa drugs to such a strain capable of producing L-lysine as mentioned above, or a strain capable of producing L-lysine obtained by endowing various nutrients requirement, a resistance to various amino acid analogs or a resistance to other chemicals as mentioned above to a strain belonging to the genus Corynebacterium and having a property of resistance to at least one member selected from the group consisting of aspartic acid analogs and sulfa drugs may also be used in the present invention. Further, the strain to be used in the present invention may have any other property of contributing to L-lysine productivity than the properties mentioned above.

Examples of aspartic acid analogs are aspartic acid hydroxamate, α-methylaspartic acid, β-methylaspartic acid, cysteinesulfinic acid, difluorosuccinic acid, hadacidin, etc. and examples of sulfa drugs are sulfaguanidine, sulfadiazine, sulfamethazine, sulfamerazine, sulfamethizole, sulfamethomidin, sulfamethoxypyridazine, sulfathiazole, homosulfamine, sulfadimethoxine, sulfamethoxazole, sulfaisoxazole, etc.

Among the strains to be used in the present invention, *Corynebacterium glutamicum* FERM-P 3633 (NRRL B-8182) may be mentioned as one example of the strain having a resistance to aspartic acid analog, and *Corynebacterium glutamicum* FERM-P 3634 (NRRL B-8183) as one example of the strain having a resistance to sulfa drugs. The strain FERM-P 3633 is a mutant obtained by suspending cells of *Corynebacterium glutamicum* ATCC 21543 having an ability to produce L-lysine (having a homoserine requirement, leucine requirement and a resistance to S-(β-aminoethyl)-cystein: see Canadian Pat. No. 937,518) in a 0.1N trismaleic acid buffer solution (pH 6.0) at a concentration of $10^8$ cells/ml, adding N-methyl-N'-nitro-N-nitrosoguanidine thereto to make a final concentration of 0.2 mg/ml, allowing the suspension to stand at room temperature for 30 minutes, then smearing the suspension on an agar plate of a minimum medium of the following composition containing 1 mg/ml of aspartic acid hydroxamate, a kind of aspartic acid analogs, and selecting the strain from growing colonies, and is clearly distinguished from the parent strain ATCC 21543 in the resistance to aspartic acid hydroxamate. Further, the strain FERM-P 3634 is a mutant selected in the same manner as described above except using an agar plate of a minimum medium containing 1 mg/ml of sulfamethazine, a kind of sulfa drugs in place of aspartic acid hydroxamate, and is distinguished from the parent strain in the resistance to sulfamethazine and sulfadiazine.

Composition of the agar plate of the minimum medium:

| | |
|---|---|
| glucose | 0.5 g/dl |
| ammonium sulfate | 0.3 g/dl |
| $KH_2PO_4$ | 0.15 g/dl |
| $K_2HPO_4$ | 0.05 g/dl |
| $MgSO_4 \cdot 7H_2O$ | 0.05 g/dl |
| $FeSO_4 \cdot 7H_2O$ | 0.001 g/dl |
| $MnSO_4 \cdot nH_2O$ | 0.001 g/dl |
| NaCl | 0.01 g/dl |
| biotin | 100 μg/l |
| vitamin $B_1$ hydrochloride | 1 mg/l |
| methionine | 50 mg/l |
| threonine | 20 mg/l |
| leucine | 200 mg/l |
| agar | 2 g/dl (pH 7.2) |

Microbiological properties of Corynebacterium glutamicum are decribed in *The Journal of General and Applied Microbiology,* 18, pages 279–301 (1967).

Any of synthetic medium and natural medium may be used as the medium for the present invention, so long as it properly contains a carbon source, nitrogen source, inorganic materials, and other necessary nutrients. As the carbon source, various carbohydrates such as glucose, fructose, sorbitol, mannitol, glycerol, starch, starch hydrolyzate, molasses, blackstrap molasses, etc., hydrocarbons such as n-paraffins, kerosene, etc., organic acids such as acetic acid, fumaric acid, lactic acid, pyruvic acid, succinic acid, etc., and alcohols such as methanol, ethanol, etc. may be used. As the nitrogen source, ammonia, inorganic and organic ammonium salts such as ammonium chloride, ammonium sulfate, ammonium phosphate, ammonium acetate, etc., urea, amines, other nitrogen-containing compounds and peptone, meat extract, yeast extract, corn steep liquor, casein hydrolyzate, fish meal, digest of fish meal, defatted soybeans, digest of defatted soybeans, soybean protein acid-hydrolyzate, various microbial cells, digest of microbial cells, etc. may be used. As the inorganic materials, potassium dihydrogen phosphate, dipotassium hydrogen phosphate, magnesium sulfate, sodium chloride, ferrous sulfate, manganese sulfate, calcium carbonate, etc. are used. When a microorganism to be used in the present invention requires specific nutrients for growth, an appropriate amount of the nutrients must, of course, be added to the medium. In some cases, these nutrients are added as components of the natural substances exemplified as the nitrogen source.

In the present invention, the productivity of L-lysine by the present microorganism can be further enhanced by adding a leucine fermentation liquor to the medium as shown in Example 3. In this case, it is preferable to add a leucine fermentation liquor in an amount ranging from 0.2 to 15% by volume of the medium.

Further, the productivity of L-lysine by the present microorganism can be also enhanced by adding other various additives, for example, various antibiotics, α-aminobutyric acid, cysteine, norleucine, leucine, aspartic acid, glutamic acid, etc. to the medium.

Culturing is carried out under aerobic conditions, for example, by shaking culture, agitation submerged culture, etc. The temperature for culturing is generally 20°–40° C., and the pH of the medium is in a range of 3 to 9, and is preferably maintained at around neutral, but culturing can be carried out under conditions which are out of this range so long as the microorganism used can grow. The pH of the medium is adjusted with calcium carbonate, organic or inorganic acid or ammonia, alkali hydroxide, pH buffering agent, etc. Usually after culturing for 1 to 7 days, L-lysine is formed and accumulated in the resulting culture liquor.

After the completion of culturing, precipitates such as cells, etc. are removed from the culture liquor, and L-lysine can be recovered by use of the conventional methods such as ion exchange resin treatment, concentration, adsorption, salting-out, etc.

Practice of specific embodiments of the invention is illustrated by the following representative examples.

EXAMPLE 1

*Corynebacterium glutamicum* FERM-P 3633, NRRL-B-8182, (having a resistance to aspartic acid hydroxamate) is used as a seed strain. The seed strain is inoculated in a large test tube of 50 ml (190 mm×20 mm) containing 7 ml of seed medium (pH 7.2) comprising 4 g/dl of glucose 0.3 g/dl of urea, 0.15 g/dl of $KH_2PO_4$, 0.05 g/dl of $K_2HPO_4$, 0.05 g/dl of $MgSO.7H_2O$, 50 μg/l of biotin, 2 g/dl of peptone, and 0.5 g/dl of yeast extract and cultured at 30° C. for 24 hours. Two ml of the resulting seed culture is inoculated in an Erylenmeyer flask of 300 ml containing 20 ml of a fermentation medium (pH 7.2) comprising 8.5 g/dl of blackstrap molasses (as glucose), 2 g/dl of soybean cake acid hydrolyzate (as soybean cake), 0.5 g/dl of ammonium sulfate, 0.3 g/dl of urea, 0.05 g/dl of $MgSO_4.7H_2O$, 0.07 g/dl of $KH_2PO_4$ and 3 g/dl of calcium carbonate, and cultured with shaking at 30° C. for 3 days. As the result, 35 mg/ml of L-lysine (as monohydrochloride, which will be hereinafter applied) is formed and accumulated in the culture liquor. Amount of L-lysine by parent strain ATCC 21543 cultured at the same time under the same conditions as a control is 25 mg/ml.

After the completion of culturing, 1 l of the culture liquor of the present strain is centrifuged to remove the cells and other precipitates. Supernatant is passed through a column of Diaion SK-1 ($H^+$ form, trade mark of strongly acidic ion exchange resin produced by Mitsubishi Chemical Industries Ltd.) to adsorb L-lysine. After washing the column with water, the column is eluted with dilute aqueous ammonia and then fractions containing L-lysine are collected and concentrated. After pH of the concentrate is adjusted to 2 by hydrochloric acid, the concentrate is cooled, while adding ethanol thereto, whereby L-lysine is crystallized. As the result, 26.5 g of crystals of L-lysine hydrochloride is obtained.

EXAMPLE 2

Culturing is carried out in the same manner as in Example 1 except that *Corynebacterium glutamicum* FERM-P 3634, NRRL-B-8183, (having a resistance to sulfamethazine) is used as a seed strain, and 33 mg/ml of L-lysine is formed and accumulated in the culture liquor. When culturing is carried out in the same manner as above with the parent strain ATCC 21543 as a control, 25 mg/ml of L-lysine is obtained.

EXAMPLE 3

*Corynebacterium glutamicum* FERM-P 3633 used in Example 1 is used as a seed strain. The seed strain is inoculated in an Erlenmeyer flask of 300 ml containing 20 ml of the seed medium as used in Example 1, and cultured with shaking at 28° C. for 24 hours. One liter of the seed culture is inoculated in a jar fermenter of 30 l containing 10 l of a fermentation medium (pH 7.2) comprising 14 g/dl of blackstrap molasses (as glucose), 0.03 g/dl of $MgSO_4.7H_2O$, 0.07 g/dl of $KH_2PO_4$, 0.3 g/dl of urea, 1.8 g/dl of soybean cake acid hydrolyzate (as soybean cake), and 1.4% (by volume) of leucine fermentation liquor prepared in advance as hereinafter described, and cultured at an aeration rate of 10 l/minute, a stirring speed of 400 r.p.m. and 28° C. for 48 hours, while adjusting pH of culture liquor at 6.8 with 22% aqueous ammonia. As the result, 58 mg/ml of L-lysine is formed and accumulated in the culture liquor. When a parent strain ATCC 21543 is cultured in the same manner as above, 43 mg/ml of L-lysine is obtained.

The leucine fermentation liquor used in said fermentation medium is prepared in the following manner. *Corynebacterium glutamicum* ATCC 21885, a leucine producing strain, is inoculated in a jar fermenter of 5 l containing 3 l of seed medium (pH 7.2) comprising 5 g/dl of glucose, 1 g/dl of peptone, 1 g/dl of yeast extract, 0.5 g/dl of corn steep liquor, 0.25 g/dl of NaCl, 0.3 g/dl of urea, and 50 µg/l of biotin, and cultured with aeration-stirring at an aeration rate of 3 l/minute, a stirring speed of 600 r.p.m. and 30° C. for 17 hours. One liter of the seed culture is inoculated in a jar fermenter of 30 l containing 10 l of a fermentation medium (pH 6.8) comprising 0.5 g/dl of ammonium acetate, 0.2 g/dl of $KH_2PO_4$, 0.05 g/dl of $MgSO_4.7H_2O$, 0.01 g/dl of $FeSO_4.7H_2O$, 0.001 g/dl of $MnSO_4.nH_2O$, 50 µg/l of biotin and 100 µg/l of thiamine hydrochloride, and cultured with aeration-stirring at an aeration rate of 10 l/minute, a stirring speed of 400 r.p.m., and 30° C. for 60 hours. In the course of culturing a mixed solution containing 7% ammonium acetate and 38% acetic acid is continuously fed to the culture liquor to supply a carbon source and to adjust the pH to 6.8. As the result, a leucine fermentation liquor containing 15.3 mg/ml of L-leucine is obtained, and used as a portion of said fermentation medium for L-lysine.

What is claimed is:

1. A process for producing L-lysine by fermentation, which comprises culturing a strain belonging to the species *Corynebacterium glutamicum* and having both an ability to produce L-lysine and a resistance to at least one member selected from the group consisting of aspartic acid hydroxamate and sulfamethazine in a nutrient medium, forming and accumulating L-lysine in the resulting culture liquor and isolating the L-lysine therefrom.

2. A process for producing L-lysine by fermentation, which comprises culturing a mutant strain belonging to the species *Corynebacterium glutamicum* and having both an improved ability to produce L-lysine and a resistance to at least one member selected from the group consisting of an aspartic acid analog selected from the group consisting of aspartic acid hydroxamate, α-methylaspartic acid, β-methylaspartic acid, cysteinesulfinic acid, difluorosuccinic acid and hadacidin and a sulfa drug selected from the group consisting of sulfaguanidine, sulfadiazine, sulfamethazine, sulfamerazine, sulfamethizole, sulfamethomidin, sulfamethoxypyridazine, sulfathizole, homosulfamine, sulfadimethoxine, sulfamethoxazole and sulfaisoxazole in a nutrient medium, forming and accumulating L-lysine in the resulting culture liquor and isolating the L-lysine therefrom.

3. A process for producing L-lysine by fermentation, which comprises culturing *Corynebacterium glutamicum* FERM-P 3633, NRRL-B-8182 or *Corynebacterium glutamicum* FERM-P 3664, NRRL-B-8183 in a nutrient medium, forming and accumulating L-lysine in the resulting culture liquor and isolating the L-lysine therefrom.

4. A process according to claim 1, wherein cultivation is effected at a temperature in the range of 20° to 40° C. and a pH in the range of 3 to 9 for a period ranging from 1 to 7 days.

5. A process according to claim 1, wherein said nutrient medium contains a leucine fermentation liquor in an amount ranging from 0.2 to 15% by volume of said nutrient medium, said leucine fermentation liquor being obtained by cultivation of a leucine producing strain of the genus Corynebacterium.

6. A process according to claim 5, wherein the leucine producing strain is *Corynebacterium glutamicum* ATCC 21885.

* * * * *